United States Patent
Wang et al.

(10) Patent No.: US 11,667,923 B2
(45) Date of Patent: Jun. 6, 2023

(54) **RECOMBINANT *CANDIDA* CELL AND PREPARATION PROCESS AND USE THEREOF**

(71) Applicant: Far Eastern New Century Corporation, Taipei (TW)

(72) Inventors: Chu-Chin Wang, Taipei (TW); Yu-Chuan Chuang, Taipei (TW); Shu-Yin Shih, Taipei (TW); Yi-Cyun Jhang, Taipei (TW)

(73) Assignee: Far Eastern New Century Corporation, Taipei (TW)

( * ) Notice: Subject to any disclaimer, the term of this patent is extended or adjusted under 35 U.S.C. 154(b) by 561 days.

(21) Appl. No.: 16/745,983

(22) Filed: Jan. 17, 2020

(65) Prior Publication Data

US 2021/0054387 A1 Feb. 25, 2021

(30) Foreign Application Priority Data

Aug. 21, 2019 (TW) .................. 108129823

(51) Int. Cl.
| | | |
|---|---|---|
| *C12N 1/19* | (2006.01) | |
| *C12P 7/56* | (2006.01) | |
| *C12N 15/81* | (2006.01) | |
| *C12N 9/22* | (2006.01) | |
| *C12N 1/16* | (2006.01) | |
| *C12R 1/72* | (2006.01) | |

(52) U.S. Cl.
CPC ............ *C12N 15/81* (2013.01); *C12N 9/22* (2013.01); *C12N 1/165* (2021.05); *C12N 2310/20* (2017.05); *C12R 2001/72* (2021.05)

(58) Field of Classification Search
None
See application file for complete search history.

(56) References Cited

U.S. PATENT DOCUMENTS

| | | | | |
|---|---|---|---|---|
| 2003/0190630 A1* | 10/2003 | Rajgarhia | ............ | C12N 9/0006 435/254.22 |
| 2004/0029256 A1* | 2/2004 | Rajgarhia | ............ | C12N 9/0006 435/254.22 |

OTHER PUBLICATIONS

Stovicek et al., "CRISPR-Cas system enables fast and simple genome editing of industrial *Saccharomyces cerevisiae* strains", Metab. Eng. Commun. 2:13-22, 2015 (Year: 2015).*

Ozaki et al., "Metabolic engineering of Schizosaccharomyces pombe via CRISPR-Cas9 genome editing for lactic acid production from glucose and cellobiose", Metab. Eng. Commun. 5:60-67, 2017 (Year: 2017).*

* cited by examiner

*Primary Examiner* — David Steadman
(74) *Attorney, Agent, or Firm* — Cesari & McKenna, LLP (57) ABSTRACT

Disclosed herein is a process for producing a recombinant *Candida* cell, which involves genetically engineering a parent *Candida* cell using a Clustered Regularly Interspaced Short Palindromic Repeats (CRISPR)/CRISPR-associated (Cas)(CRISPR/Cas) system. A recombinant *Candida* cell obtained using the process and a method for producing D-lactic acid from a biomass using the recombinant *Candida* cell are also disclosed.

6 Claims, 1 Drawing Sheet

Specification includes a Sequence Listing.

RECOMBINANT *CANDIDA* CELL AND PREPARATION PROCESS AND USE THEREOF

CROSS-REFERENCE TO RELATED APPLICATION

This application claims priority of Taiwanese Patent Application No. 108129823, filed on Aug. 21, 2019.

FIELD

The disclosure relates to a process for producing a recombinant *Candida* cell, and more particularly to a process for producing a recombinant *Candida* cell, which involves genetically engineering a parent *Candida* cell using a clustered regularly interspaced short palindromic repeats (CRISPR)/CRISPR-associated (Cas)(CRISPR/Cas) system. The disclosure also relates to a recombinant *Candida* cell capable of producing D-lactic acid via fermentable sugar consumption.

BACKGROUND

Lactic acid is the end product of glycolysis in anaerobic conditions. There are two optically active stereoisomers of lactic acid: L(+)-lactic acid and D(−)-lactic acid, which are widely used in food, cosmetic, pharmaceutical, and chemical industries.

The optical purity of lactic acid is crucial to the physical properties of poly(lactic acid) (PLA), and optically pure L(+)- or D(−)-lactic acid, rather than racemic DL-lactic acid, can be polymerized to high crystalline PLA that is suitable for commercial uses. PLA is considered both biodegradable (e.g., adapted for short-term packaging) and biocompatible in contact with living tissues (e.g., suitable for biomedical applications such as implants, sutures, drug encapsulation, etc.). PLA can be degraded by biotic degradation, i.e., simple hydrolysis of the ester bond without requiring the presence of enzymes to catalyze it. Therefore, the biotechnological production of lactic acid has received a significant amount of interest recently, since it offers an alternative to environmental pollution caused by the petrochemical industry and the limited supply of petrochemical resources.

In recent years, a number of studies aim at improving L(+)- or D(−)-lactic acid production via genetic engineering. For instance, EP 1513923 B1 discloses three recombinant *Kluyveromyces marxianus* Pdc-Lh-D-LDH strains CD587, CD589, and CD590, which are produced by replacing the endogenous pdc1 gene encoding pyruvate decarboxylase 1 (PDC1) with the exogenous d-ldh gene encoding D-lactate dehydrogenase (D-LDH) via homologous recombination. In the examples of EP 1513923 B1, the Pdc-Lh-D-LDH strains CD587, CD589, and CD590 were cultivated in 250 mL baffled shake flasks containing 50 mL YPD supplemented with 100 g/L glucose and 50 g/L CaCO3. After 54 hours, the Pdc-Lh-D-LDH strains CD587, CD589, and CD590 had consumed 85-88 g/L glucose, and produced 81 g/L lactate and 2.5 g/L pyruvate. These lactate titers represent a 92-95% lactate yield on glucose.

US 2012/0058529 A1 discloses a recombinant *Candida utilis* strain having an ability of producing L-lactic acid highly efficiently. In the examples of US 2012/0058529 A1, the recombinant *Candida utilis* strain was produced as follows. A *Candida utilis* strain was subjected to multiple disruptions of the pdc gene using the Cre-lox System to obtain a *Candida utilis* strain Cu8402g in which the endogenous pdc gene was completely disrupted. Subsequently, two copies of the l-ldh gene encoding L-lactate dehydrogenase (L-LDH) were introduced into the *Candida utilis* strain Cu8402g using the Cre-lox System, so that the aforesaid recombinant *Candida utilis* strain (such strain was designated the Pj0957 strain) was produced. The Pj0957 strain was inoculated into a medium containing 100 to 115 g/L glucose in a 100 mL baffled Erlenmeyer flask so as to conduct fermentation, and the concentration of L-lactic acid in the medium at 24 hour after the start of fermentation was determined. The experimental results indicate that the Pj0957 strain can produce L-lactic acid with high efficiency.

Ozaki A. et al. have disclosed a D-lactic acid (D-LA)-producing *Saccharomyces pombe* strain ATRS-LA1, which is constructed by subjecting a *Saccharomyces pombe* strain FY12804 to metabolic pathway engineering based on CRISPR/Cas9-mediated genome editing. The CRISPR/Cas9-mediated genome editing includes introducing the mhpF and eutE genes by integration into the pdc101 and pdc202 loci, respectively, introducing the d-ldh gene into the gpd2 locus, and deleting the l-ldh and adh (SPBC337.11) genes. The potential of the ATRS-LA1 strain for D-LA acid production was evaluated using test tube-scale fermentation. The experimental results reveal that after 55 h of cultivation, the ATRS-LA1 strain consumed glucose at 35.5 g/L and produced D-LA at 11.8 g/L, corresponding to a yield of 0.33 g D-LA/g glucose. Ozaki A. et al. have further modified the ATRS-LA1 strain by introducing a second copy of the d-ldh expression cassette by targeted disruption of the endogenous adh8 gene, yielding a strain ATRS-LA2. In a 55-h fermentation experiment, the ATRS-LA2 strain consumed glucose at 35.5 g/L and produced D-LA at 25.2 g/L, corresponding to a yield of 0.71 g D-LA/g glucose (Ozaki A. et al. (2017), *Metab. Eng. Commun.*, 5: 60-67).

In spite of the aforesaid, there is still a need to develop a more satisfactory recombinant yeast cell that can consume a biomass containing a fermentable sugar and produce D-lactic acid with high efficiency.

SUMMARY

Accordingly, in a first aspect, the present disclosure provides a process for producing a recombinant *Candida* cell, comprising:

introducing into a parent *Candida* cell a CRISPR (clustered regularly interspaced short palindromic repeats)/Cas9 (CRISPR-associated protein 9) system, so that all copies of an endogenous pdc gene of the parent *Candida* cell are replaced with an exogenous d-ldh gene, wherein the CRISPR/Cas9 system comprises:

(a) at least one guide RNA that hybridizes to the endogeneous pdc gene, the at least one guide RNA having a guide sequence selected from the group consisting of SEQ ID NO: 22, SEQ ID NO: 23, SEQ ID NO: 24, and SEQ ID NO: 25;

(b) a Cas9; and (c) a donor DNA molecule comprising a 5' homology arm, a 3' homology arm, and the exogenous d-ldh gene located between the 5' homology arm and the 3' homology arm, wherein the 5' homology arm and the 3' homology arm respectively hybridize to an upstream and a downstream of the endogenous pdc gene, so as to replace the endogenous pdc gene with the exogenous d-ldh gene through homologous recombination.

In a second aspect, the present disclosure provides a recombinant *Candida* cell which is produced by a process as described above.

In a third aspect, the present disclosure provides a method for producing D-lactic acid from a biomass, which comprises subjecting the biomass to a fermentation reaction with a recombinant *Candida* cell. The biomass contains a fermentable sugar. The recombinant *Candida* cell consumes the fermentable sugar to produce D-lactic acid. The recombinant *Candida* cell is produced by a process as described above.

BRIEF DESCRIPTION OF THE DRAWINGS

The above and other objects, features and advantages of the present disclosure will become apparent with reference to the following detailed description and the exemplary embodiments taken in conjunction with the accompanying drawings, in which.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described. For clarity, the following definitions are used herein.

The terms "nucleic acid", "nucleic acid sequence", and "nucleic acid fragment" as used herein refer to a deoxyribonucleotide or ribonucleotide sequence in single-stranded or double-stranded form, and comprise naturally occurring nucleotides or artificial chemical mimics. The term "nucleic acid" as used herein is interchangeable with the terms "gene", "cDNA", "mRNA", "oligo-nucleotide", and "poly-nucleotide" in use.

As used herein, the term "DNA fragment" refers to a DNA polymer, in the form of a separate segment or as a component of a larger DNA construct, which has been derived either from isolated DNA or synthesized chemically or enzymatically such as by methods disclosed elsewhere.

Unless otherwise indicated, a nucleic acid sequence, in addition to the specific sequences described herein, also covers its complementary sequence, and the conservative analogs, related naturally occurring structural variants and/or synthetic non-naturally occurring analogs thereof.

As used herein, the term "transformation" can be used interchangeably with the term "transfection" when such term is used to refer to the introduction of an exogenous nucleic acid molecule into a selected host cell. According to techniques known in the art, a nucleic acid molecule (e.g., a recombinant DNA construct or a recombinant vector) can be introduced into a selected host cell by various techniques, such as calcium phosphate- or calcium chloride-mediated transfection, electroporation, microinjection, particle bombardment, liposome-mediated transfection, transfection using bacterial bacteriaphages, transduction using retroviruses or other viruses (such as vaccinia virus or baculovirus of insect cells), protoplast fusion, *Agrobacterium*-mediated transformation, or other methods.

The terms "cell", "host cell", "transformed host cell", and "recombinant host cell" as used herein can be interchangeably used, and not only refer to specific individual cells but also include sub-cultured offsprings or potential offsprings thereof. Sub-cultured offsprings formed in subsequent generations may include specific genetic modifications due to mutation or environmental influences and, therefore, may factually not be fully identical to the parent cells from which the sub-cultured offsprings were derived. However, sub-cultured cells still fall within the coverage of the terms used herein.

As used herein, the terms "parent *Candida* cell" and "*Candida* mother strain" can be interchangeably used, and refer to a *Candida* cell used to conduct one or more genetic modification treatments. The parent *Candida* cells suitable for the present disclosure may be non-transformed cells or cells transformed with at least one recombinant nucleic acid.

The parent *Candida* cells suitable for the present disclosure may be cells of *Candida utilis*, cells of *Candida boidinii*, cells of *Candida tropicalis*, or cells of *Candida parapsilosis*. In one exemplary embodiment of the present disclosure, the parent *Candida* cell to be used is a cell of *Candida utilis*.

The present disclosure provides a process for producing a recombinant *Candida* cell, comprising:
introducing into a parent *Candida* cell a CRISPR (clustered regularly interspaced short palindromic repeats)/Cas9 (CRISPR-associated protein 9) system, so that all copies of an endogenous pdc gene of the parent *Candida* cell are replaced with an exogenous d-ldh gene, wherein the CRISPR/Cas9 system comprises:
(a) at least one guide RNA that hybridizes to the endogeneous pdc gene, the at least one guide RNA having a guide sequence selected from the group consisting of SEQ ID NO: 22, SEQ ID NO: 23, SEQ ID NO: 24, and SEQ ID NO: 25;
(b) a Cas9; and
(c) a donor DNA molecule comprising a 5' homology arm, a 3' homology arm, and the exogenous d-ldh gene located between the 5' homology arm and the 3' homology arm, wherein the 5' homology arm and the 3' homology arm respectively hybridize to an upstream and a downstream of the endogenous pdc gene, so as to replace the endogenous pdc gene with the exogenous d-ldh gene through homologous recombination.

According to the present disclosure, the parent *Candida* cell contains a plurality of copies of the endogenous pdc gene. In an exemplary embodiment of the present disclosure, the parent *Candida* cell contains four copies of the endogenous pdc gene.

In an exemplary embodiment of the present disclosure, the parent *Candida* cell is a cell of the *Candida utilis* strain deposited under the accession number BCRC 20325 or ATCC 9950.

As used herein, the term "guide RNA (gRNA)" refers to an RNA molecule (or a group of RNA molecules collectively) that can bind to a CRISPR protein and target the CRISPR protein to a specific location within a target DNA. A guide RNA can comprise three sequences: a guide sequence (i.e. a DNA targeting guide sequence), a tracr sequence (i.e. a protein-binding sequence), and a tracr mate sequence (which is complementary to the tracr sequence). The guide sequence comprises a nucleotide sequence that is complementary to (or at least can hybridize to under stringent conditions) a target sequence. The tracr sequence interacts with a CRISPR protein, such as a Cas9 or Cas9 related polypeptide. The guide sequence and the tracr sequence can be located in the same RNA molecule or in two or more separate RNA molecules. When the two sequences are in separate RNA molecules, the molecule comprising the guide sequence is sometimes referred to as the guide RNA, while the molecule comprising the tracr sequence is referred to as the trans-activating crRNA (tracrRNA).

According to the present disclosure, the tracrRNA may be produced using technology well-known to those skilled in the art, or may include various commercially available products, e.g., Edit-R tracrRNA (Dharmacon, Inc., Cat. No. U-002005-20), Alt-R™ CRISPR tracrRNA (Integrated DNA Technologies, Inc., Cat. No. 1072532), and SygRNA® SpCas9 tracrRNA (Merck, Inc., Cat. No. TRACRRNAOSN-SNMOL). In an exemplary embodiment of the present disclosure, the tracrRNA is Edit-R tracrRNA.

According to the present disclosure, the CRISPR/Cas9 system may comprise two of the guide RNAs. One of the guide RNAs has a guide sequence of SEQ ID NO: 22, and the other one of the guide RNAs has a guide sequence of SEQ ID NO: 25.

It is noted that the operation conditions of the CRISPR/Cas9 system may vary, depending on the guide RNA and CRISPR proteins applied, the exogenous genes to be expressed, etc. The actual operation conditions necessary for the CRISPR/Cas9 system are well known in the art, and can be determined without undue experimentation.

According to the present disclosure, the 5' homology arm, the 3' homology arm, and the exogenous d-ldh gene may be synthesized using a genetic engineering technique well-known to and commonly used by one skilled in the art, e.g. the techniques described in US 2012/0058529 A1 and US 2016/0177321 A1.

According to the present disclosure, the 5' homology arm may have a nucleotide sequence of SEQ ID NO: 16, and the 3' homology arm may have a nucleotide sequence of SEQ ID NO: 19.

According to the present disclosure, the exogenous d-ldh gene may be derived from the genome of any one of the following microorganisms: *Leuconostoc mesenteroides* subsp. *Mesenteroides*, *Lactobacillus plantarum*, *Lactobacillus delbrueckii* subsp. *bulgaricus*, *Neurospora crassa*, *Lactobacillus acidophilus*, and *Lactococcus lactis*. In an exemplary embodiment of the present disclosure, the exogenous d-ldh gene is derived from the genome of *Leuconostoc mesenteroides* subsp. *Mesenteroides*.

According to the present disclosure, the exogenous d-ldh gene may have a nucleotide sequence of SEQ ID NO: 1.

The present disclosure also provides a recombinant *Candida* cell which is produced by a process as described above.

In an exemplary embodiment of the present disclosure, the recombinant *Candida* cell is a cell of the *Candida utilis* strain D813 deposited under the accession number BCRC 920114 or CCTCC M 2019431.

The present disclosure also provides a method for producing D-lactic acid from a biomass, which comprises subjecting the biomass to a fermentation reaction with a recombinant *Candida* cell. The biomass contains a fermentable sugar. The recombinant *Candida* cell is able to produce D-lactic acid by consuming the fermentable sugar. The recombinant *Candida* cell is produced by a process as described above.

According to the present disclosure, the biomass may be a sugar liquor or a cellulosic hydrolysate.

According to the present disclosure, the cellulosic hydrolysate is prepared by performing a pretreatment and a hydrolysis treatment on a raw cellulosic biomass material in sequence.

As used herein, the terms "cellulosic hydrolysate", "lignocellulosic hydrolysate" and "biomass hydrolysate" can be used interchangeably, and refer to products generated from saccharification of biomass.

According to the present disclosure, the fermentable sugar may be selected from the group consisting of glucose, sucrose, fructose, arabinose, galactose, mannose, cellobiose, and combinations thereof.

According to the present disclosure, when a sugar liquor containing glucose is used as the biomass for the fermentation reaction, the recombinant *Candida* cell of the present disclosure may have a D-lactic acid yield of, for instance, at least about 82.5%, at least about 90%, or at least about 97.2%.

According to the present disclosure, when a sugar liquor containing sucrose is used as the biomass for the fermentation reaction, the recombinant *Candida* cell of the present disclosure may have a D-lactic acid yield of, for example, at least about 86.56%, at least about 90%, or at least about 94.32%.

According to the present disclosure, the biomass may be further added with a neutralizing agent before the fermentation reaction or during the fermentation reaction, such that the pH value of the biomass is maintained in the range of 5 to 7 during the fermentation.

According to the present disclosure, the neutralizing agent may be selected from the group consisting of $CaCO_3$, $NH_4OH$, NaOH, and combinations thereof.

In an exemplary embodiment of the present disclosure, 45 g/L $CaCO_3$ is added into the biomass during the fermentation reaction, such that the pH value of the biomass is maintained at pH 6 during the fermentation reaction.

According to the present disclosure, the fermentation reaction may be conducted at a temperature ranging from 25–37° C. for 18-60 hours.

In an exemplary embodiment of the present disclosure, the fermentation reaction is conducted at 30° C. for 48 hours.

In another exemplary embodiment of the present disclosure, the fermentation reaction is conducted at 35° C. for 22 hours.

In yet another exemplary embodiment of the present disclosure, the fermentation reaction is conducted at 35° C. for 26 hours.

According to the present disclosure, the fermentation reaction may be conducted at an aeration rate ranging from 0.1 vvm to 1 vvm.

In an exemplary embodiment of the present disclosure, the fermentation reaction is conducted at an aeration rate ranging from 0.5 vvm to 1 vvm.

In another exemplary embodiment of the present disclosure, the fermentation reaction is conducted at an aeration rate of 1 vvm.

The disclosure will be further described by way of the following examples. However, it should be understood that the following examples are solely intended for the purpose of illustration and should not be construed as limiting the disclosure in practice.

EXAMPLES

General Experimental Materials:

1. The primers for polymerase chain reaction (PCR) as used in the examples were synthesized by Mission Biotech Co., Ltd.

2. The CRISPR RNAs (crRNAs) used in the examples were synthesized by Dharmacon, Inc.

3. The *Candida utilis* strains used in the examples were all purchased from Bioresources Collection and Research Center (BCRC) of Food Industry Research and Development Institute (FIRDI) (Hsinchu City, Taiwan) and were as follows:

(1) *Candida utilis* BCRC 20325, which also has been deposited at American Type Culture Collection (ATCC, Manassas, Va., USA) under an accession number ATCC 9950;

(2) *Candida utilis* BCRC 21691, which also has been deposited at American Type Culture Collection (ATCC, Manassas, Va., USA) under an accession number ATCC 36178; and (3) *Candida utilis* BCRC 21645, which also has been deposited at Deutsche Sammlung von Mikroorganismen and Zellkulturen GmbH (Inhoffenstr. 7B, D-38124 Braunschweig, Germany) under an accession number DSM 70163.

4. Glucose was purchased from Echo Chemical Co., Ltd, peptone was purchased from ST BIO, Inc., and yeast extract was purchased from Genezyme biotech Co., Ltd.

5. $CaCO_3$, $NH_4OH$, and NaOH were all purchased from Sigma-Aldrich.

6. T4 DNA ligase was purchased from Yeastern Biotech Co., Ltd (Cat. No. FYC003).

7. The following experimental materials were purchased from Dharmacon, Inc.: trans-activating crRNA (tracrRNA) (Cat. No. U-002005-20) and Cas9 nuclease protein (Cat. No. CAS 11201).

General Procedures:

1. The experimental procedures related to DNA cloning as employed in the present disclosure, such as extraction of genomic DNA, DNA cleavage reaction by restriction enzymes, agarose gel electrophoresis, DNA ligation with T4 DNA ligase, etc., were performed by virtue of techniques well known to those skilled in the art or in accordance with the manufacturer's instructions.

2. PCR:

PCR was conducted using a KOD DNA polymerase (Merck Taiwan) in accordance with the manufacturer's instructions.

3. High performance liquid chromatography (HPLC): The components and concentration (g/L) thereof in a test sample were determined using a HPLC instrument (DIONEX Ultimate 3000) equipped with a DAD-3000 UV detector. The column and operation conditions for HPLC are as follows: SUMICHIRAL OA-6000 column; mobile phase: 2 mM $CuSO_4$/5% acetonitrile (1:156, w/w); flow rate: 0.8 mL/min; sample injection volume: 20 μL; temperature of the column oven: 38° C.; and detection wavelength at 254 nm.

Furthermore, D-lactic acid (0.5-12 mg/mL) was used as a control standard and was subjected to the same HPLC analysis.

Example 1. Preparation of Recombinant *Candida utilis* Strain Having D-Lactic Acid Production Ability In order to obtain a recombinant *Candida utilis* strain which can express an exogenous d-ldh gene and in which all copies of an endogenous pdc gene are knocked out, site-specific genome editing in *Candida utilis* using the CRISPR/Cas9 system was conducted as follows.

Experimental Procedures:

A. Preparation of Competent *Candida utilis* Cells

A YPD20 medium was prepared using the recipe shown in Table 1. A respective one of *Candida utilis* ATCC 9950, ATCC 36178, and DSM 70163 was inoculated into the YPD20 medium, followed by conducting cultivation in a shaking incubator (30° C., 200 rpm) until an $OD_{600}$ value of 1.3-1.5 (about 0.32 g cells/L) was reached.

TABLE 1

| Ingredients | Concentration (g/L) |
| --- | --- |
| Glucose | 20 |
| Yeast extract | 10 |
| Peptone | 20 |

The balance is deionized water.

After centrifugation at 6,000 g and 4° C. for 6 minutes, the resultant cell pellet was collected, followed by suspension in 10 mL of a transformation solution (containing 100 mM lithium acetate (LiAc), 10 mM Tris-HCl, and 1 mM EDTA). After incubation in a shaking incubator (30° C., 200 rpm) for 1 hour, 1 mL of 1M DTT was added and the shaking cultivation was continued for 30 minutes, followed by centrifugation at 6,000 g and 4° C. for 6 minutes.

After removal of the supernatant, the cell pellet was re-suspended in 20 mL of ice cold $ddH_2O$, followed by centrifugation at 6,000 g and 4° C. for 6 minutes. After removal of the supernatant, the cell pellet was re-suspended in 15 mL of ice cold $ddH_2O$, followed by centrifugation at 6,000 g and 4° C. for 6 minutes.

After removal of the supernatant, the cell pellet was re-suspended in 1 mL of ice cold sorbitol (1 M), followed by centrifugation at 6,000 g and 4° C. for 6 minutes. After removal of the supernatant, the cell pellet was re-suspended in 80 μL of ice cold sorbitol (1 M). The resultant bacterial suspension of the respective sorbitol-treated competent *Candida utilis* cell was dispensed into a microcentrifuge tube (70 μL/tube) and was stored at −80° C. for subsequent use.

B. Gene Synthesis of Optimized d-Ldh Gene

In order to prepare an optimized d-ldh gene that can be expressed in *Candida utilis*, the d-ldh gene of *Leuconostoc mesenteroides* subsp. *Mesenteroide* (NCBI Accession No. AB233384.1) was subjected to base optimization. Consequently, an optimized d-ldh gene, which has a nucleotide sequence of SEQ ID NO:1 (996 bp), was designed. Subsequently, the nucleotide sequence of SEQ ID NO: 1 was synthesized by Mission Biotech Co., Ltd. Thereafter, a PCR process was conducted with the resultant DNA fragment of the optimized d-ldh gene as a template and a primer pair as shown below according to the method described in section 2 of "General Procedures", so that a PCR product A1 (1,022 bp) containing the nucleotide sequence of the optimized d-ldh gene and EcoRI/XhoI restriction sites was obtained.

```
Forward primer D-LDH-PacI-F
                                        (SEQ ID NO: 2)
5'-gataccttaattaaatgaagattttgcttac-3'
     PacI
```

-continued

Reverse primer D-LDH-SalI-R
(SEQ ID NO: 3)
5'-ttgcag<u>gtcgac</u>ttaatattcaacagcaatagctg-3'
XhoI Note:
The underlined nucleotides represent the
recognition site of the restriction enzyme
indicated therebelow.

C. Cloning of PGK Terminator, PGK Promoter, and GAP Terminator

Cloning of a PGK terminator, a PGK promoter, and a GAP terminator was conducted substantially according to the method described in US 2012/0058529 A1. Briefly, a suitable amount of a culture of Candida utilis ATCC 9950 was subjected to genomic DNA extraction using UniversAll™ tissue extract buffer. Subsequently, a PCR process was conducted with the extracted genomic DNA serving as templates and the primer pairs shown in Table 2 according to the method described in section 2 of "General Procedures". Consequently, a PCR product A2 containing a PGK terminator and SalI/NotI restriction sites (906 bp), a PCR product A3 containing a PGK promoter and NotI/KpnI restriction sites (1,406 bp), and a PCR product A4 containing a GAP terminator and BamHI/BsiWI restriction sites (859 bp) were obtained.

TABLE 2

| Primer | Nucleotide sequence (5'→3') | Target DNA fragment | Size of PCR product (bp) |
|---|---|---|---|
| Forward primer PGKt-SalI-F | SalI tattaa<u>gtcgac</u>ctgcaa gctactttgtaattaaac (SEQ ID NO: 5) | PGK terminator (SEQ ID NO: 4) | 906 |
| Reverse primer PGKt-NotI-R | NotI acggta<u>gcggccgc</u>gaat tcaacatgaatgacacg (SEQ ID NO: 6) | | |
| Forward primer PGKp-NotI-F | NotI gaattc<u>gcggccgc</u>tacc gttcgtatagcatacatt atacgaagttataagctt ttgtcttttaggagcctt c (SEQ ID NO: 8) | PGK promoter (SEQ ID NO: 7) | 1,406 |
| Reverse primer PGKp-KpnI-R | KpnI acccat<u>ggtacc</u>ctttat ccgccagtatgttag (SEQ ID NO: 9) | | |
| Forward primer GAPt-BamHI-F | BamHI ttctaa<u>ggatcc</u>attgta tgactttttatttatg (SEQ ID NO: 11) | GAP terminator (SEQ ID NO: 10) | 859 |
| Reverse primer GAPt-BsiWI-R | BsiWI ttcctt<u>cgtacg</u>taccgt tcgtataatgtatgctat acgaagttatacgtgtaa tacctcaggagtcagtag (SEQ ID NO: 12) | | |

Note:
The underlined nucleotides represent the recognition site of the restriction enzyme indicated thereabove.

D. Cloning of KanMX Fragment

Cloning of a KanMX fragment was conducted substantially according to the method described in US 2016/0177321 A1. Briefly, a PCR process was conducted with a pFA6a-link-yEGFP-Kan vector (used as a template) that contains KanMX resistant gene having a nucleotide sequence of SEQ ID NO:13 and a primer pair as shown below according to the method described in section 2 of "General Procedures", so that a PCR product A5 (834 bp) containing a KanMX fragment and KpnI/BamHI restriction sites was obtained.

Forward primer KanMX-KpnI-F
(SEQ ID NO: 14)
5'-ataaag<u>ggtacc</u>atgggtaaggaaaagac-3'
KpnI Reverse primer KanMX-BamHI-R
(SEQ ID NO: 15)
5'-tacaat<u>ggatcc</u>ttagaaaaactcatcgag-3'
BamHI Note:
The underlined nucleotides represent the recognition site of the restriction enzyme indicated therebelow.

E. Cloning of PDC1 Promoter and PDC1 Terminator

The two primer pairs shown in Table 3 were used to clone the PDC1 promoter and PDC1 terminator of Candida utilis ATCC 9950 (corresponding to nucleotide residues 1660 to 2246 and nucleotide residues 4192 to 4701 of the nucleotide sequence having NCBI Accession No. AB489119.1, respectively).

TABLE 3

| Primer | Nucleotide sequence (5'→3') | Target DNA fragment | Size of PCR product (bp) |
|---|---|---|---|
| Forward primer PDC1p-ApaI-F | ApaI acatgt<u>gggccc</u>attgca caccgcacgtctg (SEQ ID NO: 17) | PDC1 promoter (SEQ ID NO: 16) | 613 |
| Reverse primer PDC1p-PacI-R | PacI caacatt<u>taattaa</u>ggta tcgattgttttag (SEQ ID NO: 18) | | |
| Forward primer PDC1t-BsiWI-F | BsiWI acggta<u>cgtacg</u>ctcccg tgtacgcgttctag (SEQ ID NO: 20) | PDC1 terminator (SEQ ID NO: 19) | 534 |
| Reverse primer PDC1t-AvrII-R | AvrII gacgtc<u>cctagg</u>atttca cctggttgaaggag (SEQ ID NO: 21) | | |

Note:
The underlined nucleotides represent the recognition site of the restriction enzyme indicated thereabove.

A suitable amount of a culture of Candida utilis ATCC 9950 was subjected to genomic DNA extraction using UniversAll™ tissue extract buffer. Subsequently, a PCR process was conducted with the extracted genomic DNA serving as templates and the primer pairs shown in Table 3 according to the method described in section 2 of "General Procedures". Consequently, a PCR product A6 containing a PDC1 promoter and ApaI/PacI restriction sites (613 bp) and a PCR product A7 containing a PDC1 terminator and BsiWI/AvrII restriction sites (534 bp) were obtained.

F. Construction of Donor DNA Molecule Containing Exogenous d-Ldh Gene

Figure 1:
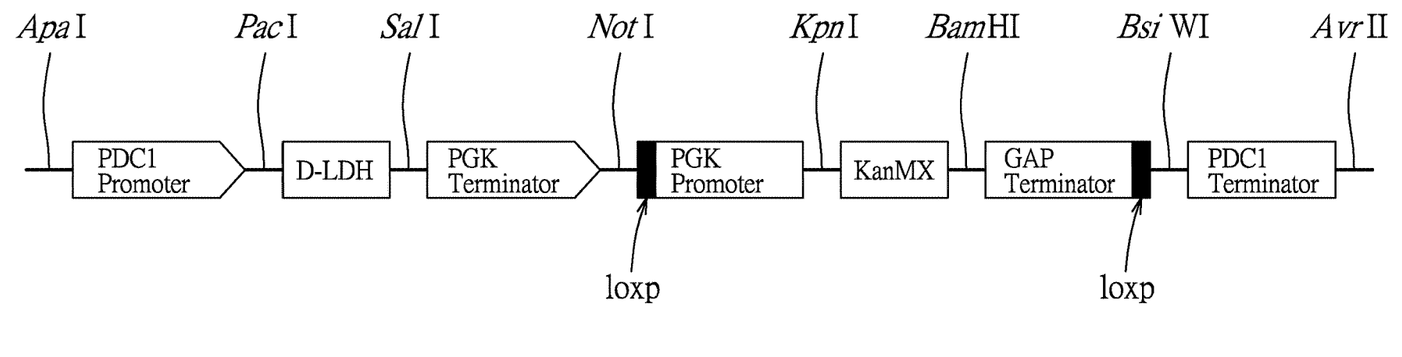
FIG. 1 is a schematic diagram of a donor DNA molecule comprising an exogenous d-ldh gene as used in an embodiment of the present disclosure.

The PCR products A1 to A7 obtained from sections B to E of this example were ligated using T4 DNA ligase, thereby obtaining a donor DNA molecule containing the exogenous d-ldh gene (6,050 bp, see FIG. 1).

G. Transformation Using CRISPR/Cas9 System

Four CRISPR RNAs (i.e. crRNA1, crRNA2, crRNA3, and crRNA4) were designed based on the complete coding sequence of the pdc1 gene of *Pichia jadinii* (which is the anamorph of *Candida utilis*) (NCBI GenBank Assession No. AB489119.1). The detailed information of the four crRNAs is summarized in Table 4.

TABLE 4

| | Target gene | Corresponding nucleotide residues in target gene | Nucleotide sequence (5'→3') |
|---|---|---|---|
| crRNA1 | pdc1 (NCBI GenBank Assession No. AB489119.1) | 2295-2276 | SEQ ID NO: 22<br>cuuguuugagucucucgaagguuuuagagcuaugcuguuuug |
| crRNA2 | | 2304-2323 | SEQ ID NO: 23<br>aacaccgucuucggucuucgguuuuagagcuaugcuguuuug |
| crRNA3 | | 2414-2395 | SEQ ID NO: 24<br>guaggcggcguucaacucguguuuuagagcuaugcuguuuug |
| crRNA4 | | 2438-2419 | SEQ ID NO: 25<br>aacucuggaguaaccaucagguuuuagagcuaugcuguuuug |

Note:
The nucleotides shown in the boxes are guide sequences, which are represented by SEQ ID NOs: 22 to 25, respectively. The nucleotides shown outside the boxes are tracr-mate sequences, which are complementary to the trans-activating crRNA (tracrRNA).

crRNA1 to crRNA4, tracrRNA, Cas9 nuclease protein, and the donor DNA molecule containing the exogenous d-ldh gene were mixed according to the recipe shown in Table 5, so that a mixture 1 and a mixture 2 were obtained.

TABLE 5

| | Contents |
|---|---|
| Mixture 1 | Donor DNA molecule (1 μg)<br>Cas9 nuclease protein (24 pmol)<br>crRNA1 (14.4 pmol)<br>crRNA4 (14.4 pmol)<br>tracrRNA (28.8 pmol) |
| Mixture 2 | Donor DNA molecule (1 μg)<br>Cas9 nuclease protein (24 pmol)<br>crRNA2 (14.4 pmol)<br>crRNA3 (14.4 pmol)<br>tracrRNA (28.8 pmol) |

Subsequently, the mixture 1 was transformed into a respective one of the competent *Candida utilis* ATCC 9950, ATCC 36178, and DSM 70163 obtained from section A of this example by virtue of electroporation (0.75 kV, 25 μF, and 800Ω). Thereafter, screening was conducted using a YPD solid medium containing an appropriate antibiotic concentration (200 μg/mL G418) so as to obtain three transformants, i.e., *Candida utilis* transformant A (which was derived from *Candida utilis* ATCC 9950), *Candida utilis* transformant B (which was derived from *Candida utilis* ATCC 36178), and *Candida utilis* transformant C (which was derived from *Candida utilis* DSM 70163).

Further, the mixture 2 was transformed into the competent *Candida utilis* ATCC 9950 according to the method described above, so as obtain a transformant, i.e., *Candida utilis* transformant D.

Afterward, 691 distinct colonies of the *Candida utilis* transformant A were selected, 490 distinct colonies of the *Candida utilis* transformant B were selected, 199 distinct colonies of the *Candida utilis* transformant C were selected, and 200 distinct colonies of the *Candida utilis* transformant D were selected. A respective one of the selected colonies was inoculated into the YPD20 medium containing 200 μg/mL G418, followed by conducting cultivation in a shaking incubator (30° C., 200 rpm). A suitable amount of a culture of the colony of the respective transformant was subjected to genomic DNA extraction using UniversAll™ tissue extract buffer. Subsequently, a PCR process was conducted with the extracted genomic DNA serving as templates and a primer pair shown in Table 6 according to the method described in section 2 of "General Procedures". To determine whether a PCR product having a size of about 784 bp was obtained, 1% agarose gel electrophoresis was performed after the PCR process was accomplished.

TABLE 6

| Primer | Nucleotide sequence (5'→3') | Corresponding nucleotide residues in target gene | Target gene | Size of PCR product (bp) |
|---|---|---|---|---|
| Forward primer PDC1-1-F | atgagcga aatcacat tgggac (SEQ ID NO: 26) | 2247-2268 | pdc1 (NCBI GenBank Assession No. AB489119.1) | 784 |
| Reverse primer PDC1-784-R | caccaccg aatcttgg gtgttgtt c (SEQ ID NO: 27) | 3030-3006 | | |

The absence of the PCR product having 784 bp indicates that all the copies of the endogenous pdc gene of the *Candida utilis* transformant have been completely replaced with the exogenous d-ldh gene, and such *Candida utilis* transformant is called successful strain of transformant.

The percent knock-out efficiency (%) was calculated using the following Equation (I):

$$A=(B/C)\times 100 \quad (I)$$

where A=percent knock-out efficiency (%)
B=number of successful strain of transformant A, B, C, or D
C=total number of transformant A, B, C, or D

TABLE 7

|  | Transformant A | Transformant B | Transformant C | Transformant D |
| --- | --- | --- | --- | --- |
| Number of successful strain of transformant | 45 | 4 | 2 | 1 |
| Total number of transformant | 691 | 490 | 199 | 200 |
| Percent knock-out efficiency (%) | 6.5 | 0.8 | 1 | 0.5 |

Table 7 shows the percent knock-out efficiency of the transformants A, B, C, and D. It can be seen from Table 7 that the *Candida utilis* can be effectively transformed with mixture 1 or mixture 2 using CRISPR/Cas9 system. Particularly, the percent knock-out efficiency of the transformant A is significantly higher than that of each of transformants B, C, and D.

H. Screening of *Candida utilis* Transformant Having D-Lactic Acid Production Ability 39 strains were randomly selected from the 45 successful strains of transformant A obtained in section G of this example. Each selected strain was inoculated into a 50 mL tube containing 10 mL of a YPD60 medium supplemented with 1% yeast extract, 2% peptone and 6% glucose, followed by cultivation in a shaking incubator (30° C., 200 rpm) for 48 hours. Subsequently, the resultant fermented culture of each selected strain (about 0.9-1.2 mL) was subjected to centrifugation at 12,000 rpm for 5 minutes to obtain a supernatant, which was then subjected to an HPLC analysis according to the method set forth in section 3 of "General Procedures" so as to determine the D-lactic acid content in the supernatant.

The D-lactic acid yield (%) of each selected successful strain of *Candida utilis* transformant was calculated using the following formula (II):

$$D=(E/F)\times 100 \quad (II)$$

where D=D-lactic acid yield (%)
E=D-lactic acid content detected in supernatant (g)
F=glucose content in fermentation medium before fermentation (g)

The D-lactic acid yield (%) of the selected successful strains of *Candida utilis* transformant A is shown in Table 8. It can be seen from Table 8 that each selected successful strains of *Candida utilis* transformant A can efficiently produce D-lactic acid via consumption of glucose. Particularly, strain D813 of *Candida utilis* transformant A exhibits the highest D-lactic acid yield. In view of the foregoing, strain D813 of *Candida utilis* transformant A has been deposited in the Biosource Collection and Research Center (BCRC) of Food Industry Research and Development Institute (FIRDI) (331 Shih-Pin Road, Hsinchu City 300, Taiwan, R.O.C.) under accession number BCRC 920114 on Apr. 22, 2019, and also has been deposited under the terms of the Budapest Treaty on the International Recognition of the Deposit of Microorganisms for the Purpose of Patent Procedure at the International Strain Depositary China Center for Type Culture Collection (CCTCC) (Wuhan University, Wuhan, 430072, People's Republic of China) under accession number CCTCC M 2019431 on Jun. 5, 2019.

TABLE 8

| Successful strain of Transformant A | D-lactic acid yield (%) | Successful strain of Transformant A | D-lactic acid yield (%) |
| --- | --- | --- | --- |
| D701 | 45.3 | D723 | 59.1 |
| D702 | 54.1 | D726 | 55.2 |
| D703 | 45.5 | D801 | 52.0 |
| D704 | 60.6 | D802 | 45.8 |
| D705 | 65.1 | D803 | 44.5 |
| D707 | 63.5 | D804 | 50.3 |
| D708 | 60.9 | D805 | 60.0 |
| D709 | 62.8 | D807 | 64.0 |
| D710 | 53.1 | D808 | 56.1 |
| D711 | 52.8 | D809 | 60.6 |
| D712 | 63.9 | D811 | 67.5 |
| D713 | 53.1 | D812 | 62.7 |
| D714 | 51.1 | D813 | 82.5 |
| D716 | 67.7 | D814 | 35.3 |
| D717 | 61.3 | D815 | 38.6 |
| D718 | 59.2 | D816 | 44.9 |
| D719 | 48.4 | D817 | 43.2 |
| D720 | 68.3 | D818 | 40.4 |
| D721 | 58.8 | D819 | 42.5 |
| D722 | 44.2 | — | — |

Example 2. Effect of Large-Scale Culture of *Candida utilis* Strain CCTCC M 2019431 on D-Lactic Acid Yield The cell culture of *Candida utilis* strain CCTCC M 2019431 (i.e. strain D813 of *Candida utilis* transformant A) obtained from section H of example 1 was inoculated into 100 mL of a fermentation medium as shown in Table 9 at a concentration of $2\times 10^8$ cell/mL, followed by conducting fermentation in a constant-temperature shaking incubator (35° C., 80 rpm) under an aerobic condition for 26 hours.

TABLE 9

| Ingredients | Concentration (g/L) |
| --- | --- |
| Glucose | 105 |
| Yeast extract | 10 |
| Peptone | 20 |
| CaCO$_3$ | 45 |

The balance is deionized water.

Afterwards, the fermentation culture of *Candida utilis* strain CCTCC M 2019431 was subjected to determination of D-lactic acid yield according to the method set forth in section H of Example 1.

The experimental results reveal that the D-lactic acid yield of *Candida utilis* strain CCTCC M 2019431 is 97.2%.

Example 3. Effect of Various Fermentation Conditions on D-Lactic Acid Yield of *Candida utilis* Strain CCTCC M 2019431

A. Effect of Neutralizing Agent on D-Lactic Acid Yield

The cell culture of *Candida utilis* strain CCTCC M 2019431 obtained from section H of example 1 was divided into four groups including a control group and three experimental groups (i.e., experimental groups 1 to 3). The cell culture of the respective group was inoculated into 2 L of a YPD60 medium as set forth in section H of Example 1, followed by conducting cultivation in a fermentor (FIRSTEK Co., Ltd., Taiwan) (30° C., 400 rpm, 0.1 vvm aeration rate) until an $OD_{600}$ value of 10 (about $2\times10^8$ cell/mL) was reached.

After centrifugation at 6,000 g for 6 minutes, the resultant cell pellet was collected, and was then inoculated into a fermentation medium (2 L) as shown in Table 10, followed by conducting cultivation in a fermentor (35° C., 250 rpm, 1 vvm aeration rate) for 22 hours. For experimental groups 1 to 3, during the fermentation, 45 g/L $CaCO_3$, 250 g/L $NH_4OH$, and 5 N NaOH were respectively added to maintain the pH value in the range of 5 to 7.

TABLE 10

| Ingredients | Concentration (g/L) |
| --- | --- |
| Glucose | 110 |
| Yeast extract | 10 |
| Peptone | 20 |

The balance is deionized water.

Afterwards, the fermentation culture of each group was subjected to determination of D-lactic acid yield according to the method set forth in section H of Example 1.

The D-lactic acid yields of the control group and the experimental groups are shown in Table 11. It can be seen from Table 11 that the D-lactic acid yield of each experimental group is higher than that of the control group. The results indicate that the neutralizing agents used for adjusting the pH value of the fermentation medium are capable of effectively enhancing the D-lactic acid yield. In particular, $CaCO_3$ achieves the highest D-lactic acid yield.

TABLE 11

| Group | Neutralizing agent | D-lactic acid yield (%) |
| --- | --- | --- |
| Control group | — | 57.09 ± 1.41 |
| Experimental group 1 | $CaCO_3$ | 95.64 ± 0.51 |
| Experimental group 2 | $NH_4OH$ | 90.80 ± 0.06 |
| Experimental group 3 | NaOH | 86.90 ± 1.03 |

B. Effect of Aeration Rate on D-Lactic Acid Yield

The cell culture of *Candida utilis* strain CCTCC M 2019431 obtained from section H of example 1 was divided into three experimental groups (i.e., experimental groups 1 to 3). The cell culture of each group was subjected to preparation of seed culture, fermentation, determination of D-lactic acid content and calculation of D-lactic acid yield generally according to the procedures described in the abovementioned section A of this example, except that each group was added with 45 g/L $CaCO_3$ to adjust the pH value, and the aeration rates of experimental groups 1 to 3 were 0.5 vvm, 0.75 vvm, and 1 vvm, respectively.

The D-lactic acid yields of the experimental groups 1 to 3 are shown in Table 12. It can be seen from Table 12 that the D-lactic acid yield of each experimental group is more than 92%. The results indicate that the fermentation can produce D-lactic acid very efficiently under an aeration rate ranging from 0.1 vvm to 1 vvm.

TABLE 12

| Group | Aeration rate (vvm) | D-lactic acid yield (%) |
| --- | --- | --- |
| Experimental group 1 | 0.5 | 92.80 ± 1.44 |
| Experimental group 2 | 0.75 | 92.98 ± 0.15 |
| Experimental group 3 | 1 | 95.92 ± 0.40 |

C. Effect of Temperature and Fermentable Sugar on D-Lactic Acid Yield

The cell culture of *Candida utilis* strain CCTCC M 2019431 obtained from section H of example 1 was divided into two experimental groups (i.e., experimental groups 1 and 2). The cell culture of each group was subjected to preparation of seed culture, fermentation, determination of D-lactic acid content and calculation of D-lactic acid yield generally according to the procedures described in the abovementioned section A of this example, except that each group was added with 45 g/L $CaCO_3$ to adjust the pH value, the fermentation medium of each group contained sucrose (100 g/L) instead of glucose, and the temperatures applied in the fermentation of experimental groups 1 and 2 were 30° C. and 35° C., respectively.

The D-lactic acid yields of the experimental groups 1 and 2 are shown in Table 13. It can be seen from Table 13 that when the fermentation is carried out at a temperature of 30° C. or 35° C. and using sucrose (100 g/L) as a fermentable sugar, the D-lactic acid yield of each experimental group is more than 86%.

TABLE 13

| Group | Temperature (° C.) | Fermentable sugar | D-lactic acid yield (%) |
| --- | --- | --- | --- |
| Experimental group 1 | 30 | Sucrose (100 g/L) | 86.56 ± 0.36 |
| Experimental group 2 | 35 | Sucrose (100 g/L) | 94.32 ± 0.58 |

Summarizing the above test results, it is clear that when the fermentation is carried out at a temperature of 35° C. and at an aeration rate of 1 vvm, using $CaCO_3$ to adjust the pH value of the fermentation medium, *Candida utilis* strain CCTCC M 2019431 of the present disclosure can efficiently produce D-lactic acid via consumption of glucose or sucrose.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A recombinant *Candida* cell, wherein the recombinant *Candida* cell is *Candida utilis* strain D813 having China Center for Type Culture Collection (CCTCC) deposit number M 2019431.

2. A method for producing D-lactic acid from a biomass, comprising:
fermentation of a biomass with the recombinant *Candida* cell of claim 1, wherein the biomass comprises a fermentable sugar, and wherein the recombinant *Candida* cell consumes the fermentable sugar to produce D-lactic acid.

3. The method of claim 2, wherein the fermentable sugar is selected from the group consisting of glucose, sucrose, fructose, arabinose, galactose, mannose, cellobiose, and combinations thereof.

4. The method of claim 2, wherein the biomass further comprises a neutralizing agent selected from the group consisting of $CaCO_3$, $NH_4OH$, NaOH, and combinations thereof.

5. The method of claim 2, wherein the fermentation is conducted at a temperature ranging from 25° C. to 37° C.

6. The method of claim 2, wherein the fermentation is conducted at an aeration rate ranging from 0.1 vvm to 1 vvm.

* * * * *

SEQUENCE LISTING

<160> NUMBER OF SEQ ID NOS: 27

<210> SEQ ID NO 1
<211> LENGTH: 996
<212> TYPE: DNA
<213> ORGANISM: Artificial Sequence
<220> FEATURE:
<223> OTHER INFORMATION: The optimized d-ldh gene

<400> SEQUENCE: 1

```
atgaagattt ttgcttacgg tattagagat gatgaaaagc catcattgga agaatggaaa      60
gctgctaacc cagagattga agttgactac acacaagagt tgttgacacc tgaaacagtt     120
aagttggctg agggatcaga ttcagctgtt gtttaccaac aattggacta tacaagagaa     180
acattgacag ctttagctaa cgttggtgtt actaacttgt cattgagaaa cgttggtaca     240
gataacattg attttgatgc agcaagagaa tttaacttta cattcaaa tgttcctgtt      300
tattcaccaa atgctattgc agaacactca atgattcaat tatctaggtt gttgagaaga     360
actaaagcat ggatgccaa aattgctaag cacgacttga atgggcacc aacaattgga      420
agagaaatga aatgcaaac agttggtgtt attggtacag tcatattgg tagagttgct      480
attaacattt tgaaaggttt tggtgcaaag gttattgctt atgataagta cccaaatgct     540
gaattgcaag cagaaggttt gtacgttgac acattgacg aattatatgc acaagctgat     600
gcaatttcat tgtatgttcc tggtgttcct gaaaaccatc atttgatcaa tgcagaggct     660
attgctaaga tgaaggatgg tgttgttatc atgaatgctg ctagaggtaa tttgatggac     720
attgatgcta ttattgatgg tttaaattct ggtaagattt cagacttcgg tatggacgtt     780
tatgaaaatg aagttggttt gttcaatgaa gattggtctg gtaaagaatt tccagatgct     840
aagattgctg acttgatttc aagagaaaat gtattggtta ctccacatac tgctttctat     900
acaactaaag ctgttttgga aatggttcac caatcatttg atgcagcagt tgctttcgcc     960
aaaggtgaga agccagctat tgctgttgaa tattaa                               996
```

<210> SEQ ID NO 2
<211> LENGTH: 32
<212> TYPE: DNA
<213> ORGANISM: Artificial Sequence
<220> FEATURE:
<223> OTHER INFORMATION: Forward primer D-LDH-PacI-F for PCR amplification of the optimized d-ldh gene

<400> SEQUENCE: 2

```
gataccttaa ttaaatgaag atttttgctt ac                                    32
```

<210> SEQ ID NO 3
<211> LENGTH: 35
<212> TYPE: DNA
<213> ORGANISM: Artificial Sequence
<220> FEATURE:
<223> OTHER INFORMATION: Reverse primer D-LDH-SalI-R for PCR amplification of the optimized d-ldh gene

<400> SEQUENCE: 3

```
ttgcaggtcg acttaatatt caacagcaat agctg                                 35
```

<210> SEQ ID NO 4
<211> LENGTH: 880
<212> TYPE: DNA
<213> ORGANISM: Candida utilis

<400> SEQUENCE: 4

-continued

```
ctgcaagcta ctttgtaatt aaacaaataa cgggattata tgtcaatatc attatgatta      60
tttaggaaaa catgtagacc ttacccgatg cacctccacc aacaagccaa ttctgggtgg     120
gatggaagtt acacactgct ggtacgttgg tcaccagtgg gtttgacaaa tgtgccagct     180
gatgaccatc tcggtcgtag acgtcaaagt acttgttcat attggcaatg acaaactttt     240
ctttgtccgg ggtatattgc tgccaccttg ccttcaaaat ggatacccat cttcccgttt     300
gacaattgtg tttgatacga tgacttgggg tcaaatcacc ttcaatagcg aagttcttag     360
gtttagtgct gatgtcctca ccaagattga agatgttaac tgtgtcatcg taaccgttac     420
aaacaaggtc accagatcta ttccaatcca cgatggaaac tgacaatctt gaatcataga     480
cgccaacagt gtgcagagtc tccaggttgt catcccattc atcccaatca cacgtagttg     540
ctgttcttag atcccaaacc ttcaaagttc gatccaatga ggcagtagca atctggttct     600
tattcatcgg attgatagtg aatccaccaa tctttttatt cgacaatctc aaaacttgtc     660
ttcttgagtg atcgcctgct ctcaggtcaa ttctgctgaa ttgtccttgc attgttgtgt     720
agtacatttc attgtcgttg ttgtaattta tgtcagtgat accgacgtca aagtcgttga     780
tgaataactg tgaggacttc atggagcgta gatcaattga gcgaatggac ccatcatacg     840
atgcactgta gaccttcgtc gtgtcattca tgttgaattc                           880
```

<210> SEQ ID NO 5
<211> LENGTH: 36
<212> TYPE: DNA
<213> ORGANISM: Artificial Sequence
<220> FEATURE:
<223> OTHER INFORMATION: Forward primer PGKt-SalI-F for PCR
      amplification of PGK terminator

<400> SEQUENCE: 5

```
tattaagtcg acctgcaagc tactttgtaa ttaaac                                36
```

<210> SEQ ID NO 6
<211> LENGTH: 35
<212> TYPE: DNA
<213> ORGANISM: Artificial Sequence
<220> FEATURE:
<223> OTHER INFORMATION: Reverse primer PGKt-NotI-R for PCR
      amplification of PGK terminator

<400> SEQUENCE: 6

```
acggtagcgg ccgcgaattc aacatgaatg acacg                                 35
```

<210> SEQ ID NO 7
<211> LENGTH: 1346
<212> TYPE: DNA
<213> ORGANISM: Candida utilis

<400> SEQUENCE: 7

```
aagcttttgt cttttaggag ccttcttttc accctggctt tcttcagact ccacgcctct      60
cgcccgtttg ttgttgatct tcttctgttg cttcttcgtg agcttaccag tatccagatg     120
cgttgtcagg gcaagagggt catgttcaag ctcctctttc actttcagtc caatacgttt     180
ccaggcaggg atgtgttcgc tcatcgttcc agactcgagt ggtgaaaact atggcaacct     240
ctacttcctt tccaaacaca cagcgtgctt tgtagtgtgt gcctaagagc tgaattttt      300 ttccttccat gctgcgctgc gatgagctct gcccgcccgc agcctcggag gctagcgacg     360
tataaaaaag gcctgtgaaa attttatcct cctccttaac gacccttctt tctcttcttc     420
```

```
acattcaaaa acttcaagca gctgtctctg ttcctttgct gtgttctacc attggatatt      480
cccattcccc gtggagaacc gaactggagt ctagcagcat gcgagatcaa tattacacgg      540
tttgagtctg atacgcttga gcagccattt tttggcttct cctggtgtgt atccagatat      600
agaagttcgt atacatttcc catagcgatt gtaaaatgat tctgcaatgg aaccatccgt      660
aattgtaggc ctgctgagat ggcactcgca atgcctctgt gtctggtttt ttgccttctc      720
cgtccatcag caccagtggc ttcttagggc ataacgagac ggctccttgg tgaaagatgc      780
cctgctccgt ctgtctgcct gttgctacaa ccactgcgta gtcagatgac ccggtctgtg      840
tgctgtggaa tcaccgggag cgaaattccg gtttcgctgg cagatgagct catcaaccac      900
atcaactgga gcaacctcac cagaggacac gtaacctgcc cggttgaatt ctgtcaaacc      960
gtacatcaca caacaacagc agcagcaaca acaacaacgt cagttgtcgt tcgcatggcg     1020
acgttaccta acggcaccaa catcgtctcg tcctcgccaa tgcctgtttc ccctacccgg     1080
agtggcccgg cccacctgtc gttctttttt cgtcaattgt gtccagctgg tgccatcacc     1140
atatgttcaa gtgcgtggcc tgtactagcg cagtctgctg cagtataaaa gggattgctg     1200
aggccccctt tagcgtttcc aattaacaat tgattccctt ttccccatag tccgtttgta     1260
ctacatccta cataacaaaa gtgagtgtta caagacaagt gtggcggtca attggatcat     1320
ttggactaac atactggcgg ataaag                                           1346
```

<210> SEQ ID NO 8
<211> LENGTH: 73
<212> TYPE: DNA
<213> ORGANISM: Artificial Sequence
<220> FEATURE:
<223> OTHER INFORMATION: Forward primer PGKp-NotI-F for PCR
      amplification of PGK promoter

<400> SEQUENCE: 8

```
gaattcgcgg ccgctaccgt tcgtatagca tacattatac gaagttataa gcttttgtct      60
tttaggagcc ttc                                                          73
```

<210> SEQ ID NO 9
<211> LENGTH: 33
<212> TYPE: DNA
<213> ORGANISM: Artificial Sequence
<220> FEATURE:
<223> OTHER INFORMATION: Reverse primer PGKp-KpnI-R for PCR
      amplification of PGK promoter

<400> SEQUENCE: 9

```
acccatggta ccctttatcc gccagtatgt tag                                    33
```

<210> SEQ ID NO 10
<211> LENGTH: 801
<212> TYPE: DNA
<213> ORGANISM: Candida utilis

<400> SEQUENCE: 10

```
attgtatgac tttatttat gggattacgt tataaattat gatcctcatg gattatctta       60
ttaagtctcc atcttgtagc ttgtaatatg atgaacactc gtgagttttc caggtaattc      120
accgtgcctc gtccatgcac ttttatcagc ctcgacgtca tacattgcat ggtgagtaac      180
tggaaaacgg cttttacgt tctgttgtat atggctaaac gcttctatgg cacggcgcta      240
ttaacctgtc tgacatttca acctggtgtt gatggcttaa acgataatac ggtgagatat      300
atagctaaca gaatggggggt gacgcactga ttccactgta tatataggcg atatgtgttg      360
```

```
ttggatggac gtttctttgt ctcctgatcc acaatagtag ctcagctccg tgccaactgg    420
ttcgctggta cgatagtgag ggatgaatga aaccttttcg ttttcttctg cgcttccacg    480
gaactgtgta gatttctctc gtgaatagcg agttaagcca cgagtggggt ctgcaattga    540
aggtgtgata ccagagtcaa aagtttggat gtgatggaaa cttcaaaggc ttctcggtgg    600
tatatcaaac gattcacaga ggtagaagcg gatcttgaag gccagaatat gcattaaaac    660
cagcgtatat cagttttctt tcccagagag gacttttgca ttattcttca gctttatccc    720
tggattttgg gagatgaaac attgacaaag ctggttcgtg atcctaaata cttgcctact    780
gactcctgag gtattacacg t                                              801
```

```
<210> SEQ ID NO 11
<211> LENGTH: 33
<212> TYPE: DNA
<213> ORGANISM: Artificial Sequence
<220> FEATURE:
<223> OTHER INFORMATION: Forward primer GAPt-BamHI-F for PCR
      amplification of GAP terminator

<400> SEQUENCE: 11
ttctaaggat ccattgtatg acttttattt atg                                 33
```

```
<210> SEQ ID NO 12
<211> LENGTH: 72
<212> TYPE: DNA
<213> ORGANISM: Artificial Sequence
<220> FEATURE:
<223> OTHER INFORMATION: Reverse primer GAPt-BsiWI-R for PCR
      amplification of GAP terminator

<400> SEQUENCE: 12
ttccttcgta cgtaccgttc gtataatgta tgctatacga agttatacgt gtaataccte    60 aggagtcagt ag                                                        72
```

```
<210> SEQ ID NO 13
<211> LENGTH: 810
<212> TYPE: DNA
<213> ORGANISM: Artificial Sequence
<220> FEATURE:
<223> OTHER INFORMATION: KanMX resistance gene

<400> SEQUENCE: 13
atgggtaagg aaaagactca cgtttcgagg ccgcgattaa attccaacat ggatgctgat    60
ttatatgggt ataaatgggc tcgcgataat gtcgggcaat caggtgcgac aatctatcga    120
ttgtatggga agcccgatgc gccagagttg tttctgaaac atggcaaagg tagcgttgcc    180
aatgatgtta cagatgagat ggtcagacta aactggctga cggaatttat gcctcttccg    240
accatcaagc attttatccg tactcctgat gatgcatggt tactcaccac tgcgatcccc    300
ggcaaaacag cattccaggt attagaagaa tatcctgatt caggtgaaaa tattgttgat    360
gcgctggcag tgttcctgcg ccggttgcat tcgattcctg tttgtaattg tccttttaac    420
agcgatcgcg tatttcgtct cgctcaggcg caatcacgaa tgaataacgg tttggttgat    480
gcgagtgatt ttgatgacga gcgtaatggc tggcctgttg aacaagtctg gaaagaaatg    540
cataagcttt tgccattctc accggattca gtcgtcactc atggtgattt ctcacttgat    600
aaccttattt ttgacgaggg gaaattaata ggttgtattg atgttggacg agtcggaatc    660
gcagaccgat accaggatct tgccatccta tggaactgcc tcggtgagtt ttctccttca    720
```
ttacagaaac ggctttttca aaaatatggt attgataatc ctgatatgaa taaattgcag        780
tttcatttga tgctcgatga gtttttctaa                                        810

<210> SEQ ID NO 14
<211> LENGTH: 29
<212> TYPE: DNA
<213> ORGANISM: Artificial Sequence
<220> FEATURE:
<223> OTHER INFORMATION: Forward primer KanMX-KpnI-F for PCR
      amplification of KanMX resistance gene

<400> SEQUENCE: 14 ataaaggta ccatgggtaa ggaaaagac                                           29

<210> SEQ ID NO 15
<211> LENGTH: 30
<212> TYPE: DNA
<213> ORGANISM: Artificial Sequence
<220> FEATURE:
<223> OTHER INFORMATION: Reverse primer KanMX-BamHI-R for PCR
      amplification of KanMX resistance gene

<400> SEQUENCE: 15
tacaatggat ccttagaaaa actcatcgag                                         30

<210> SEQ ID NO 16
<211> LENGTH: 587
<212> TYPE: DNA
<213> ORGANISM: Candida utilis

<400> SEQUENCE: 16
attgcacacc gcacgtctgt gcagtttgcc atcaatcgac gtttatagca cacaccatag         60
atcacacaga gcttcggctc tattccgttc cgtagagaaa agcaaccatt gtatacaaac        120
accaaggcta tcgcttcccg attcgtcaaa tgcacagctt cccttcaggt ggcccagctg        180
agcgcaacat gaaaaccggt cctgcgcaca ctttatccaa gcatgtggat ggcaccatgc        240
ggttaaaaac tatgcactta tgcaacgata cgggcacgat ttgaatgagt tgaacacaca        300
cacgcgtagc acacactggt ttatgcctgg ttaagcagtg ccctctgtat tcgctgtctg        360
cgtcaaatgg tgtcaaaagg actaaaagga attttttagga aagggggagt ggtcagttgt      420
taccgttgtc gtcttacata tataagaagc tagggtttcc cactttgctc tgagcgtagg        480
aatgtttcaa ctcatcatca tctattacag gaaactcaat tgaatcatca ttttcaattg        540
atacccgtta tacacaacaa acaaacaaaa ctaaaacaat cgatacc                     587

<210> SEQ ID NO 17
<211> LENGTH: 31
<212> TYPE: DNA
<213> ORGANISM: Artificial Sequence
<220> FEATURE:
<223> OTHER INFORMATION: Forward primer PDC1p-ApaI-F for PCR
      amplification of PDC1 promoter

<400> SEQUENCE: 17
acatgtgggc ccattgcaca ccgcacgtct g                                       31

<210> SEQ ID NO 18
<211> LENGTH: 31
<212> TYPE: DNA
<213> ORGANISM: Artificial Sequence
<220> FEATURE:
<223> OTHER INFORMATION: Reverse primer PDC1p-PacI-R for PCR
      amplification of PDC1 promoter

```
<400> SEQUENCE: 18
caacatttaa ttaaggtatc gattgtttta g                                  31

<210> SEQ ID NO 19
<211> LENGTH: 510
<212> TYPE: DNA
<213> ORGANISM: Candida utilis

<400> SEQUENCE: 19
ctcccgtgta cgcgttctag ttaaccattt ttttatgttt tctgccgtcc actttgatct    60
acgttgaagt taaggaacct ttacattgtt ggatttagcc ccttacgctc cctttgtttc   120
acactactag agctggcgct gctgaagatc ctattcaatc catattgatc cagaaacgat   180
aaccgcatag cgagcgctga aagagctgga aaaagataga ggagaaaaca cagctttgtt   240
cttcgcttga gacaaagaca taagtaactg gtgctttcac gagactgctt gggggttatt   300
gttgctgtag ttttgttgtc tactcgagct cgctccgttt cgtcatttac cgctgttttt   360
aactttgcaa tagtccgtgt gtgtgtgtgt tcgtattaac agttaatgtg tggaaaatgg   420
ttcctggaat caacaagcag aagctcgtga atacaacgag acagtattta cacgctgtga   480
acatgaattt ctccttcaac caggtgaaat                                    510

<210> SEQ ID NO 20
<211> LENGTH: 32
<212> TYPE: DNA
<213> ORGANISM: Artificial Sequence
<220> FEATURE:
<223> OTHER INFORMATION: Forward primer PDC1t-BsiWI-F for PCR
      amplification of PDC1 terminator

<400> SEQUENCE: 20
acggtacgta cgctcccgtg tacgcgttct ag                                 32

<210> SEQ ID NO 21
<211> LENGTH: 32
<212> TYPE: DNA
<213> ORGANISM: Artificial Sequence
<220> FEATURE:
<223> OTHER INFORMATION: Reverse primer PDC1t-AvrII-R for PCR
      amplification of PDC1 terminator

<400> SEQUENCE: 21
gacgtcccta ggatttcacc tggttgaagg ag                                 32

<210> SEQ ID NO 22
<211> LENGTH: 20
<212> TYPE: RNA
<213> ORGANISM: Artificial Sequence
<220> FEATURE:
<223> OTHER INFORMATION: Guide sequence for crRNA1

<400> SEQUENCE: 22
cuuguuugag ucucucgaag                                               20

<210> SEQ ID NO 23
<211> LENGTH: 20
<212> TYPE: RNA
<213> ORGANISM: Artificial Sequence
<220> FEATURE:
<223> OTHER INFORMATION: Guide sequence for crRNA2

<400> SEQUENCE: 23
```

```
aacaccgucu ucggucuucc                                                   20

<210> SEQ ID NO 24
<211> LENGTH: 20
<212> TYPE: RNA
<213> ORGANISM: Artificial Sequence
<220> FEATURE:
<223> OTHER INFORMATION: Guide sequence for crRNA3

<400> SEQUENCE: 24
guaggcggcg uucaacucgu                                                   20

<210> SEQ ID NO 25
<211> LENGTH: 20
<212> TYPE: RNA
<213> ORGANISM: Artificial Sequence
<220> FEATURE:
<223> OTHER INFORMATION: Guide sequence for crRNA4

<400> SEQUENCE: 25
aacucuggag uaaccaucag                                                   20

<210> SEQ ID NO 26
<211> LENGTH: 22
<212> TYPE: DNA
<213> ORGANISM: Artificial Sequence
<220> FEATURE:
<223> OTHER INFORMATION: Forward primer PDC1-1-F for PCR amplification
      of pdc gene

<400> SEQUENCE: 26
atgagcgaaa tcacattggg ac                                                22

<210> SEQ ID NO 27
<211> LENGTH: 25
<212> TYPE: DNA
<213> ORGANISM: Artificial Sequence
<220> FEATURE:
<223> OTHER INFORMATION: Reverse primer PDC1-784-R for PCR amplification
      of pdc gene

<400> SEQUENCE: 27
caccaccgaa tcttgggtgt tgttc                                             25
```